United States Patent
Qin et al.

(10) Patent No.: US 10,731,326 B2
(45) Date of Patent: Aug. 4, 2020

(54) URINE AUTOMATIC POSITIONING METHOD AND DEVICE, AND HEALTHY SMART TOILET CONTAINING SAME

(71) Applicant: Shanghai Kohler Electronics, Ltd., Shanghai (CN)

(72) Inventors: Zhiyu Qin, Beijing (CN); Qintao Sun, Beijing (CN)

(73) Assignee: SHANGHAI KOHLER ELECTRONICS, LTD., Shanghai (CN)

( * ) Notice: Subject to any disclaimer, the term of this patent is extended or adjusted under 35 U.S.C. 154(b) by 56 days.

(21) Appl. No.: 16/097,229

(22) PCT Filed: Oct. 25, 2016

(86) PCT No.: PCT/CN2016/103184
§ 371 (c)(1),
(2) Date: Oct. 26, 2018

(87) PCT Pub. No.: WO2017/185689
PCT Pub. Date: Nov. 2, 2017

(65) Prior Publication Data
US 2019/0093332 A1    Mar. 28, 2019

(30) Foreign Application Priority Data
Apr. 28, 2016 (CN) .......................... 2016 1 0273915

(51) Int. Cl.
*E03D 11/13* (2006.01)
*E03D 11/00* (2006.01)
(Continued)

(52) U.S. Cl.
CPC ............ *E03D 11/13* (2013.01); *A61B 10/007* (2013.01); *E03D 9/00* (2013.01); *E03D 11/00* (2013.01)

(58) Field of Classification Search
CPC ....... A61B 10/007; E03D 11/00; E03D 11/13; E03D 9/00
See application file for complete search history.

(56) References Cited

U.S. PATENT DOCUMENTS

| 4,870,252 A * | 9/1989 | Balmer | ................ G05D 22/02 392/446 |
|---|---|---|---|
| 6,892,402 B2 | 5/2005 | Lim | |

(Continued)

FOREIGN PATENT DOCUMENTS

| CN | 102724938 | 10/2012 |
|---|---|---|
| CN | 102995735 | 3/2013 |

(Continued)

OTHER PUBLICATIONS

PCT International Preliminary Report on Patentability re PCT/CN2016/103184; 5 pages.

(Continued)

*Primary Examiner* — Marcus H Taningco
(74) *Attorney, Agent, or Firm* — Foley & Lardner LLP

(57) ABSTRACT

A device/method for automatically positioning urine, which determines the position of the urine according to a temperature result scanned by a non-contact temperature sensor, and calculates point coordinates of the position of the urine in a toilet. The device/method includes one or more positioning assemblies with each having the sensor, a stepping motor, and a motor frame, with the sensor being fixed to a main shaft of the stepping motor, the stepping motor being fixed to the motor frame, and the motor frame configured to be fixed to the toilet. The device/method are configured for use with toilets so that the position of the urine is determined by temperature scanned by the sensor, and the urine sample is absorbed in the air as a health analysis sample, preventing cross-contamination between, urine samples absorbed from (Continued)

inner surfaces of the toilet and improving the accuracy of the health data analysis.

20 Claims, 7 Drawing Sheets

(51) Int. Cl.
    *A61B 10/00*     (2006.01)
    *E03D 9/00*     (2006.01)

(56) References Cited

U.S. PATENT DOCUMENTS

| | | | |
|---|---|---|---|
| 9,756,297 B1 * | 9/2017 | Clements | G06K 9/00771 |
| 2005/0258258 A1 * | 11/2005 | Jonte | B05B 12/087 236/12.15 |

FOREIGN PATENT DOCUMENTS

| | | |
|---|---|---|
| CN | 104771266 | 7/2015 |
| CN | 104840140 | 8/2015 |
| CN | 104963395 | 10/2015 |
| CN | 105804189 | 7/2016 |
| CN | 205604388 | 9/2016 |
| JP | 09159441 | 6/1997 |
| JP | 2008249672 | 10/2008 |
| JP | 2012017548 A * | 1/2012 |
| JP | 2015114181 A * | 6/2015 |

OTHER PUBLICATIONS

PCT International Search Report and Written Opinion re PCT/CN2016/103184; 9 pages.

* cited by examiner

URINE AUTOMATIC POSITIONING METHOD AND DEVICE, AND HEALTHY SMART TOILET CONTAINING SAME

CROSS-REFERENCE TO RELATED PATENT APPLICATIONS

This application is a US National Stage of International Application No. PCT/CN2016/103184, filed Oct. 25, 2016, which claims the benefit and priority of Chinese Patent Application No. 201610273915.9, filed Apr. 28, 2016, both of which are incorporated herein by reference in their entireties.

TECHNICAL FIELD

The present invention relates to the field of smart toilet, and particularly to a method and device for automatically positioning urine, and a healthy smart toilet containing the same.

BACKGROUND

As the people's living standard continues to rise, smart toilet has gradually stepped into people's life. In addition to satisfying the comfort requirements, the smart toilet is additionally provided with a health monitoring function, such as making a health data analysis through collecting urine sample. However, cross-contamination may occur when using urine samples collected from an inner surface of the toilet, which affects the accuracy of the health data analysis. Therefore, at present, how to avoid the cross-contamination between urine samples absorbed from the inner surface of the toilet to improve the accuracy of the health data analysis has become an urgent problem to be solved.

SUMMARY

A first technical problem to be solved by the present invention is to provide a method for automatically positioning urine, used for a healthy smart toilet. In this method, the urine can be positioned while it is in the air before contacting the toilet, therefore the urine can be collected without contacting the toilet. This method prevents the cross-contamination between urine samples and improves the accuracy of the health data analysis.

The present invention uses the following technical solutions in order to solve the above-mentioned technical problems.

A method for automatically positioning urine, comprising: determining a position of the urine according to a temperature result scanned by a non-contact temperature sensor, and calculating point coordinates of the position of the urine in a toilet.

Further, the method comprises: step A: scanning and detecting temperature by sector scanning within an angle $\gamma$ using the non-contact temperature sensor arranged in a left or right side wall of the toilet, the non-contact temperature sensor is driven by a stepping motor; calculating X in point coordinates (X, Y) of the position of the urine in the toilet based on the angle with the highest temperature and tangent formula; and/or step B: scanning and detecting temperature within an angle $\delta$ by sector scanning using the non-contact temperature sensor arranged in a front or rear side wall of the toilet, the non-contact temperature sensor is driven by a stepping motor, and calculating Y in point coordinates (X, Y) of the position of the urine in the toilet based on the angle with the highest temperature and tangent formula.

Further, the step A specifically comprises: step A1: when the sensor scans within the angle $\gamma$, each time the stepping motor turns by an angle $\varphi$, the sensor reads temperature and records the highest temperature value and the turning angle $\lambda$ of the stepping motor at which the highest temperature value is read; and step A2: calculating the position of the urine each time the sensor reaches the boundary of the angle $\gamma$.

Step B specifically comprises: step B1: when the sensor scans within the angle $\delta$, each time the stepping motor turns by an angle $\theta$, the sensor reads temperature and records the highest temperature value and the turning angle $\omega$ of the stepping motor at which the highest temperature value is read; and step B2: calculating the position of the urine each time the sensor reaches the boundary of the angle $\delta$.

Further, in the step A2, the calculation method is $X=(L1/\cos \mu)*\tan(|\gamma/2-\lambda|)$; wherein, L1 is the distance between the long shaft of the toilet and the central scanning point of the left or right side wall where the sensor is located, and $\mu$ is an included angle between a scanning plane of the sensor and the horizontal plane; and in the step B2, the calculation method is $Y=(L2/\cos \xi)*\tan(|\delta/2-\omega|)$; wherein, L2 is the distance between the short shaft of the toilet and the central scanning point of the front or rear side wall where the sensor is located, and $\xi$ is an included angle between a scanning plane of the sensor and the horizontal plane.

Further, in the steps A1 and B1, when the sensor reads temperature, the lowest temperature value is recorded meanwhile; and in the steps A2 and B2, each time the sensor reaches the boundary, a temperature difference between the highest temperature and the lowest temperature is calculated, and if the temperature difference is greater than a set temperature difference threshold, the position of the mine is calculated.

Further, in the steps A1 and B1, the entire scanning area is divided into N sectors; and in the steps A2 and B2, each time the sensor reaches the lower boundary of one sector, a temperature difference between the highest temperature and the lowest temperature of the sector is calculated, and if the temperature difference is greater than the set temperature difference threshold, the position of the urine is calculated.

Further, prior to step A, scanning is firstly conducted in the scope of the angle $\gamma$ or angle $\delta$, the lowest environment temperature in the scope of the angle $\gamma$ or angle $\delta$ is recorded, and different temperature difference thresholds are set according to different lowest environment temperatures; or the temperature difference thresholds are directly set as 3° C.

Further, the sensor has three modes comprising full-angle scanning, small-angle scanning and extended-scope scanning, within the angle $\gamma$ and the angle $\delta$; the full-angle scanning reads temperature within the entire angle $\gamma$ and angle $\delta$; each scanning area is divided into N sectors, the small-angle scanning reads temperature in the scope of a center sector and its adjacent sectors on both left and right sides; and the extended-scope scanning reads temperature in the scope of a center sector and its adjacent two sectors on both left and right sides; before the position of the urine is found for the first time, the sensor conducts the full-angle scanning; when the position of the urine is found, the sensor conducts the small-angle scanning in the sector where the urine is found and the adjacent sectors on both left and right sides; when the sensor conducts a small-angle scanning, if none of the sectors presents a temperature difference greater than the temperature difference threshold, which indicates that the position of the urine is changed, the extended-scope scanning is conducted by the sensor in the scope of the sector where the urine is originally found and adjacent two sectors on both left and right sides; and if none of the sectors presents a temperature difference greater than the temperature difference threshold during the extended-scope scanning, the sensor conducts a full-angle scanning again.

Additionally, a second technical problem to be solved by the present invention is to provide a device for automatically positioning urine in a healthy smart toilet. In this device, the urine can be positioned while it is in the air before contacting the toilet, therefore the urine can be collected without contacting the toilet, which prevents the cross-contamination between urine samples.

The present invention uses the following technical solutions in order to solve the above-mentioned technical problems.

A device for automatically positioning urine, comprising a module for automatically positioning urine, configured to determine the position of the urine according to a temperature result scanned by a non-contact temperature sensor, and calculate point coordinates of the position of the urine in a toilet.

Further, the module for automatically positioning urine comprises a first module for scanning, recording and position calculating, configured to scan and detect temperature by sector scanning within an angle $\gamma$ using the non-contact temperature sensor arranged in a left or right side wall of the toilet, the non-contact temperature sensor is driven by a stepping motor, and calculate X in point coordinates (X, Y) of the position of the urine in the toilet based on the angle with the highest temperature and tangent formula; and/or a second module for scanning, recording and position calculating, configured to scan and detect temperature by sector scanning within an angle $\delta$ using the non-contact temperature sensor arranged in a front or rear side wall of the toilet, the non-contact temperature sensor is driven by the stepping motor, and calculate Y in point coordinates (X, Y) of the position of the urine in the toilet based on the angle with the highest temperature and tangent formula.

Further, the first module for scanning, recording and position calculating specifically comprises: a first module for scanning and recording, configured to: when the sensor scans within the angle $\gamma$, read temperature each time the stepping motor turns by an angle $\varphi$, and record the highest temperature value and the turning angle $\gamma$ of the stepping motor at which the highest temperature value is read; and a first module for position calculating, configured to calculate the position of the urine each time the sensor reaches the boundary of the angle.

The second module for scanning, recording and position calculating specifically comprises: a second module for scanning and recording, configured to: when the sensor scans within the angle $\delta$, read temperature each time the stepping motor turns by an angle $\theta$, and record the highest temperature value and the turning angle $\omega$ of the stepping motor at which the highest temperature value is read; and a second module for position calculating, configured to calculate the position of the urine when the sensor reaches the boundary of the angle $\delta$.

Further, in the first module for position calculating, the calculation method is $X=(L1/COS\ \mu)*TAN(|\gamma/2-\lambda|)$; wherein, L1 is the distance between the long shaft of the toilet and the central scanning point of the left or right side wall where the sensor is located, and $\mu$ is the included angle between a scanning plane of the sensor and the horizontal plane; and in the second module for position calculating, the calculation method is $Y=(L2/COS\ \xi)*TAN(|\delta/2-\omega|)$; wherein, L2 is the distance between the short shaft of the toilet and the central scanning point of the front or rear side wall where the sensor is located, and $\xi$ is the included angle between a scanning plane of the sensor and the horizontal plane.

Further, in the first and second modules for scanning and recording, when the sensor reads temperature, the lowest temperature value is recorded meanwhile; and in the first and second modules for position calculating, each time the sensor reaches the boundary, a temperature difference between the highest temperature and the lowest temperature is calculated, and if the temperature difference is greater than the set temperature difference threshold, the position of the urine is calculated.

Further, in the first and second modules for scanning and recording, the entire scanning area is divided into N sectors; and in the first and second modules for position calculating, each time the sensor reaches the lower boundary of one sector, a temperature difference between the highest temperature and the lowest temperature of the sector is calculated, and if the temperature difference is greater than the set temperature difference threshold, the position of the urine is calculated.

The device for automatically positioning urine further comprises a module for setting temperature difference threshold, wherein scanning is firstly conducted in the scope of the angle $\gamma$ or angle $\delta$, the lowest environment temperature in the scope, of the angle $\gamma$ or angle $\delta$ is recorded, and different temperature difference thresholds are set according to different lowest environment temperatures; or the temperature difference threshold is directly set as 3° C.

The device for automatically positioning urine further comprises a module for setting temperature difference threshold, wherein scanning is firstly conducted in the scope of the angle $\gamma$ or angle $\delta$, the lowest environment temperature in the scope of the angle $\gamma$ or angle $\delta$ is recorded, and different temperature difference thresholds are set according to different lowest environment temperatures; or the temperature difference threshold is directly set as 3° C.

Further, in the module for automatically positioning urine, the sensor has three modes comprising full-angle scanning, small-angle scanning and extended-scope scanning, within angle $\gamma$ and angle $\delta$; the full-angle scanning reads temperature within the entire angle $\gamma$ and angle $\delta$; each scanning area is divided into N sectors, the small-angle scanning reads temperature in the scope of a center sector and its adjacent sectors on both left and right sides; and the extended-scope scanning reads temperature in the scope of a center sector and its adjacent two sectors on both left and right sides; before the position of the urine is found for the first time, the sensor conducts the full-angle scanning; when the position of the urine is found, the sensor conducts the small-angle scanning in the scope of the sector where the urine is found and the adjacent sectors on both left and right sides; when the sensor conducts a small-angle scanning, if none of the sectors presents a temperature difference greater than the temperature difference threshold, which indicates that the position of the urine is changed, the extended-scope scanning is conducted by the sensor in the scope of the sector where the urine is originally found and adjacent two sectors on both left and right sides; and if none of the sectors presents a temperature difference greater than the temperature difference threshold during the extended-scope scanning, the sensor conducts a full-angle scanning again.

A device for automatically positioning urine comprises one or more sets of positioning assemblies in the sense of physical structure, wherein the positioning assembly comprises a non-contact temperature sensor, a stepping motor and a motor frame; the non-contact temperature sensor is fixed to the main shaft of the stepping motor, the stepping motor is fixed to the motor frame, and the motor frame is used for fixing to the toilet; and the stepping motor can drive the non-contact temperature sensor to conduct sector scanning.

The positioning assembly further comprises an optocoupler connected to the non-contact temperature sensor and used for determining a zero point of polar coordinates of the sensor.

A third technical problem to be solved by the present invention is to provide a healthy smart toilet containing a device for automatically positioning urine. In the healthy smart toilet, urine can be positioned while it is in the air before contacting the toilet, therefore the urine can be collected without contacting the toilet, which prevents the cross-contamination between urine samples.

The present invention uses the following technical solutions in order to solve the above-mentioned technical problems.

A healthy smart toilet comprises a toilet body, and further comprises the device for automatically positioning urine as described above in the section on the physical structure, wherein the device for automatically positioning urine is mounted on the toilet body, and the stepping motor can drive the non-contact temperature sensor to conduct sector scanning.

Further, two sets of the positioning assemblies are provided, one set is mounted on a front or rear side wall of the toilet body, and the other set is mounted on a left or right side wall of the toilet body.

The present invention at least has the following, advantages by use of the above-mentioned designs.

1. In the present invention, point coordinates of the urine are determined by use of temperature (urine temperature, or urine temperature and environment temperature), so that the urine absorbed while being in air is used as the sample for health analysis, avoiding the cross-contamination when absorbing the urine sample from the inner surface of the toilet and thus improving the accuracy of the health data analysis.

2. By using the non-contact temperature sensor with the stepping motor to conduct sector scanning and by determining point coordinates using tangent formula, a new positioning method is provided, which is simple and practical with small error that can be neglected.

3. With two scanning areas in cooperation and using tangent formula to achieve positioning by point coordinates (X, Y), positioning accuracy is improved.

4. Positioning accuracy and positioning efficiency are improved by calculating temperature difference based on the full-angle scanning.

5. Positioning accuracy is improved by setting multiple sectors and conducting comparison calculation at the lower boundary of the sector.

6. The problem of position change of urine is solved by conducting the full-angle scanning in cooperation with the small-angle scanning or the extended-scope scanning.

7. Positioning accuracy can be improved by scanning firstly and determining the lowest environment temperature in the scanning scope, and then setting different temperature difference thresholds according to the lowest environment temperature.

BRIEF DESCRIPTION OF THE FIGURES

The foregoing description is merely a summary of the technical solutions of the present invention. To understand the technical means of the present invention more clearly, the present invention is further described in detail with reference to the drawings and the detailed embodiments hereinafter.

DETAILED DESCRIPTION

The present invention provides a method for automatically positioning urine in a healthy smart toilet, which mainly comprises: based on a phenomenon that a temperature of urine is higher than an environment temperature, conducting scans for the urine by a non-contact temperature sensor when the toilet is in use, determining a position of the urine according to a temperature result scanned, and calculating the coordinates of the position points of the urine in the toilet. By this method, urine can be positioned while it is in the air, therefore the urine can be collected without contacting the toilet. This method prevents the cross-contamination between urine samples and improves the accuracy of the health data analysis. Preferably, the non-contact temperature sensor is an infrared temperature sensor.

According to the temperature positioning principle above, either a horizontal and vertical straight-line scanning mode, or a sector scanning mode can be used.

Figure 1:
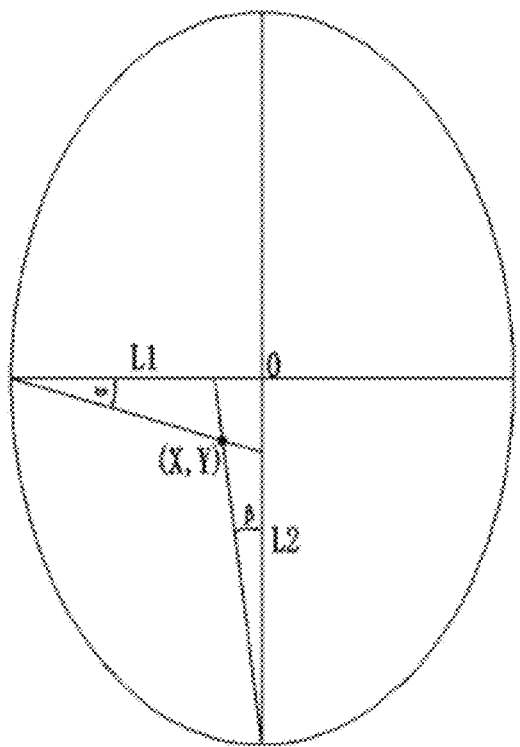
FIG. 1 is a schematic diagram of the position of urine in a toilet.
Figure 13A:
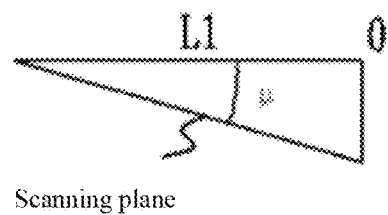
FIGS. 13a and 13b are schematic diagrams of included angles between a scanning plane and a horizontal plane.
Figure 13B:
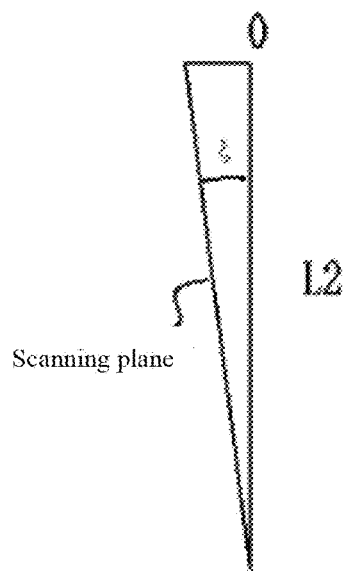

As shown in FIG. 1, the sector scanning mode mainly comprises scanning and detecting temperature by sector scanning within an angle γ using a non-contact temperature sensor arranged in a left or right side wall of the toilet and driven by a stepping motor, and calculating, based on the angle with the highest temperature and tangent formula, X in point coordinates (X, Y) of the position of the urine in the toilet; the Y value can be left undetermined, and the urine can be collected directly by a urine receiving device moving along a long shaft of the toilet. In order to further determine the position of urine more accurately, the Y in the coordinate point of the urine can be determined, the method for determining Y is similar to the method for determining X, which comprises scanning and detecting temperature by sector scanning within an angle δ using a non-contact temperature sensor arranged in a front or rear side wall of the toilet and driven by a stepping motor, and calculating, based on the angle with the highest temperature and tangent formula, the Y value in the point coordinates (X, Y) of the position of urine in the toilet. In the point coordinates (X, Y), $X=(L1/COS\ \mu)*TAN(\alpha)$, $Y=(L2/COS\ \xi)*TAN(\Theta)$, wherein L1 is the distance between the long shaft of the toilet and the central scanning point of the left or right side wall where the sensor is located, L2 is a distance between a short shaft of the toilet and a central scanning point of the front or rear side wall where the sensor is located, $\mu$ and $\xi$ are the angles between a scanning plane of the sensor and a horizontal plane (as shown in FIGS. 13*a* and 13*b*). The error in the calculation formula is small and can be neglected. The $\mu$ and $\xi$ above can be 0 degree.

Preferably, two sensors are used, one sensor is arranged at a center position of the left or right side wall of the toilet to calculate the X in the point coordinates (X, Y), and the other sensor is arranged at a center position of the front or rear side wall of the toilet to calculate the Y in the point coordinates (X, Y). The positions above are only preferred positions, and the two sensors can also be arranged at other positions.

Detailed description is conducted by taking the sector scanning mode as an example.

Embodiment 1

Figure 2:
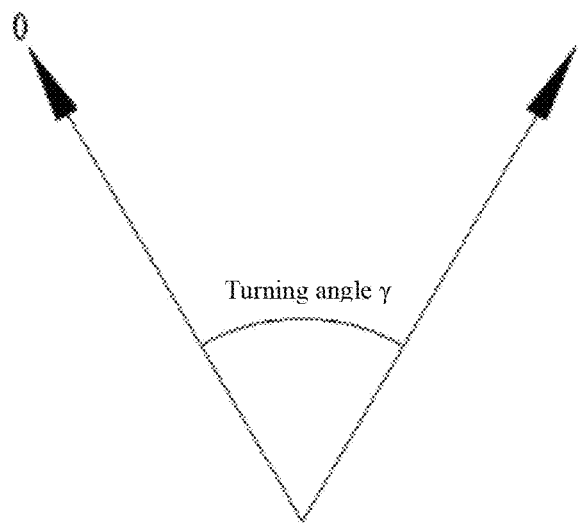
FIG. 2 is a schematic diagram of a sector scanning scope.

A sensor is mounted and fixed on the main shaft of a stepping motor, the sensor scans with the main shaft of the stepping motor within an angle $\gamma$, as shown in FIG. 2. Preferably, the scanning is conducted in a scope of 60 degrees. When the sensor scans within the angle $\gamma$, each time the stepping motor turns by an angle $\varphi$, the temperature is read by the sensor. The highest temperature value and the turning angle $\lambda$ of the stepping motor at which the highest temperature value is read are recorded, wherein $\lambda$ is equal to an integral multiple of the angle $\varphi$, and a preferred value of the angle $\varphi$ is 0.04*frequency*stepping angle.

Figure 3:
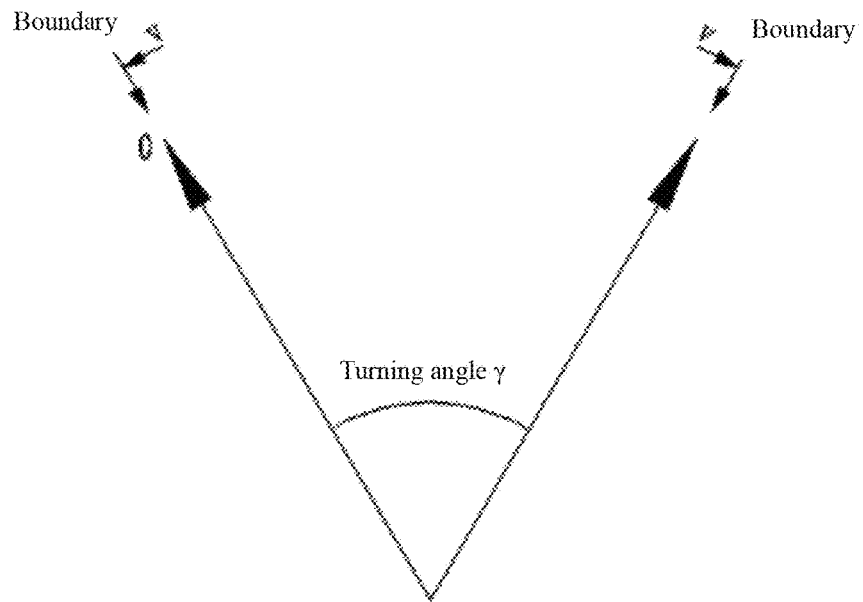
FIG. 3 is a schematic diagram of scanning boundaries (clockwise and counterclockwise)

The position of the urine is calculated each time the sensor reaches the boundary of the angle $\gamma$, as shown in FIG. 3. $\alpha=|\gamma/2-\lambda|$, and $X=(L1/COS\ \mu)*TAN(|\gamma/2-\lambda|)$. Similarly, it can be calculated that $\beta=|\delta/2-\omega|$, and $Y=(L2/COS\ \xi)*TAN(|\delta/2-\omega|)$.

Embodiment 2

A sensor is mounted and fixed on the main shaft of a stepping motor, the sensor scans with the main shaft of the stepping motor within an angle $\gamma$, as shown in FIG. 2.

When the sensor scans within the angle $\gamma$, the temperature is read by the sensor each time the stepping motor turns by an angle $\varphi$, and the highest temperature value, the lowest temperature value and the turning angle $\gamma$ of the stepping motor at which the highest temperature value is read are recorded.

A temperature difference between the highest temperature and the lowest temperature of the sector is calculated each time the sensor reaches the boundary of the angle $\gamma$, as shown in FIG. 3. If the temperature difference is greater than 3° C., the position of the urine is calculated. Experiments show that the accuracy of calculating position of urine is higher when the temperature difference is greater than 3° C. $\alpha=|\gamma/2-\lambda|$, and $X=(L1/COS\ \mu)*TAN(|\gamma/2-\lambda|)$. Similarly, it can be calculated that $\beta=|\delta/2-\omega|$, and $Y=(L2/COS\ \xi)*TAN(|\delta/2-\omega|)$.

Embodiment 3

A sensor is mounted and fixed on the main shaft of a stepping motor, the sensor scans with the main shaft of the stepping motor within an angle $\gamma$, as shown in FIG. 2.

Figure 4:
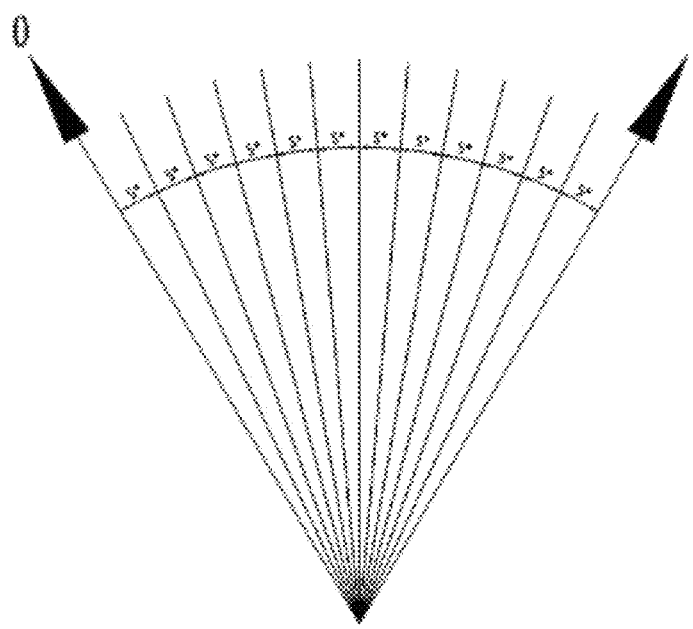
FIG. 4 is a schematic diagram of sector division.

In the angle $\gamma$, every 5 degrees are defined as one sector, and the entire angle $\gamma$ is divided into N sectors, as shown in FIG. 4. Experiments show that the calculation efficiency is higher when one sector includes 5 degrees.

When the sensor scans within the angle $\gamma$, temperature is read by the sensor each time the stepping motor turns by an angle $\varphi$, and the highest temperature value, the lowest temperature value and the turning angle $\lambda$ of the stepping motor at which the highest temperature value is read are recorded.

Figure 5:
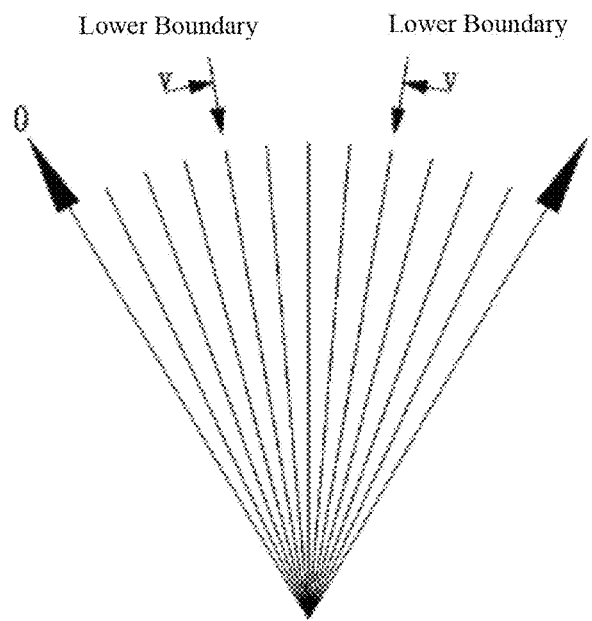
FIG. 5 is a schematic diagram of lower boundaries of the sectors (clockwise and counterclockwise)

A temperature difference between the highest temperature and the lowest temperature of the sector is calculated each time the sensor reaches the lower boundary of a sector, as shown in FIG. 5. If the temperature difference is greater than 3° C., the position of the urine is calculated. $\alpha=|\gamma/2-\lambda|$, and $X=(L1/COS\ \mu)*TAN(|\gamma/2-\lambda|)$. Similarly, it can be calculated that $\beta=|\delta/2-\omega|$, and $Y=(L2/COS\ \xi)*TAN(|\delta/2-\omega|)$.

When the position of the urine is changed, the sensor needs to re-determine the position of the urine.

Figure 6:
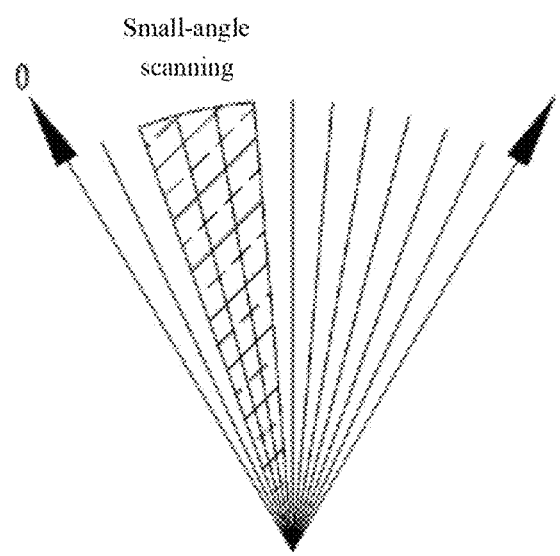
FIG. 6 is a schematic diagram of small-angle scanning.
Figure 7:
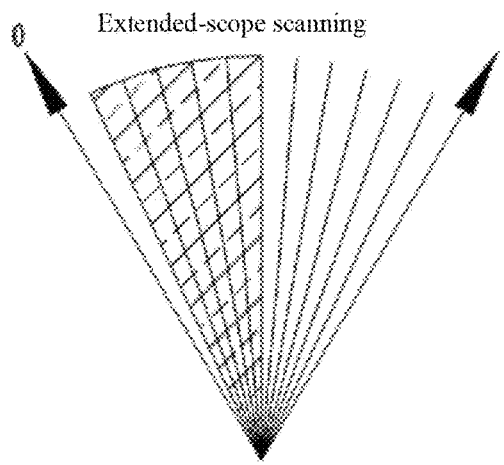
FIG. 7 is a schematic diagram of extended-scope scanning.

The sensor has three modes comprising full-angle scanning, small-angle scanning and extended-scope scanning, in the angle $\gamma$. The full-angle scanning reads the temperature in the entire angle $\gamma$. The small-angle scanning reads temperature in the scope of a center sector and its adjacent sectors on both left and right sides, as shown in FIG. 6. The extended-scope scanning reads temperature in the scope of a center sector and its adjacent two sectors on both left and right sides, as shown in FIG. 7.

Before the position of the urine is found for the first time, the sensor conducts the full-angle scanning.

When the position of the urine is found, the sensor conducts the small-angle scanning in the scope of the sector where the urine is found and the adjacent sectors on both left and right sides.

When the sensor conducts the small-angle scanning, if none of the sectors presents a temperature difference greater than the temperature difference threshold, which indicates that the position of the urine is changed, the sensor conducts the extended-scope scanning in the scope of the center sector where the urine is originally found and adjacent two sectors on both left and right sides.

If none of the sectors presents a temperature difference greater than the temperature difference threshold during the extended-scope scanning, the sensor conducts a full-angle scanning again.

Figure 8:
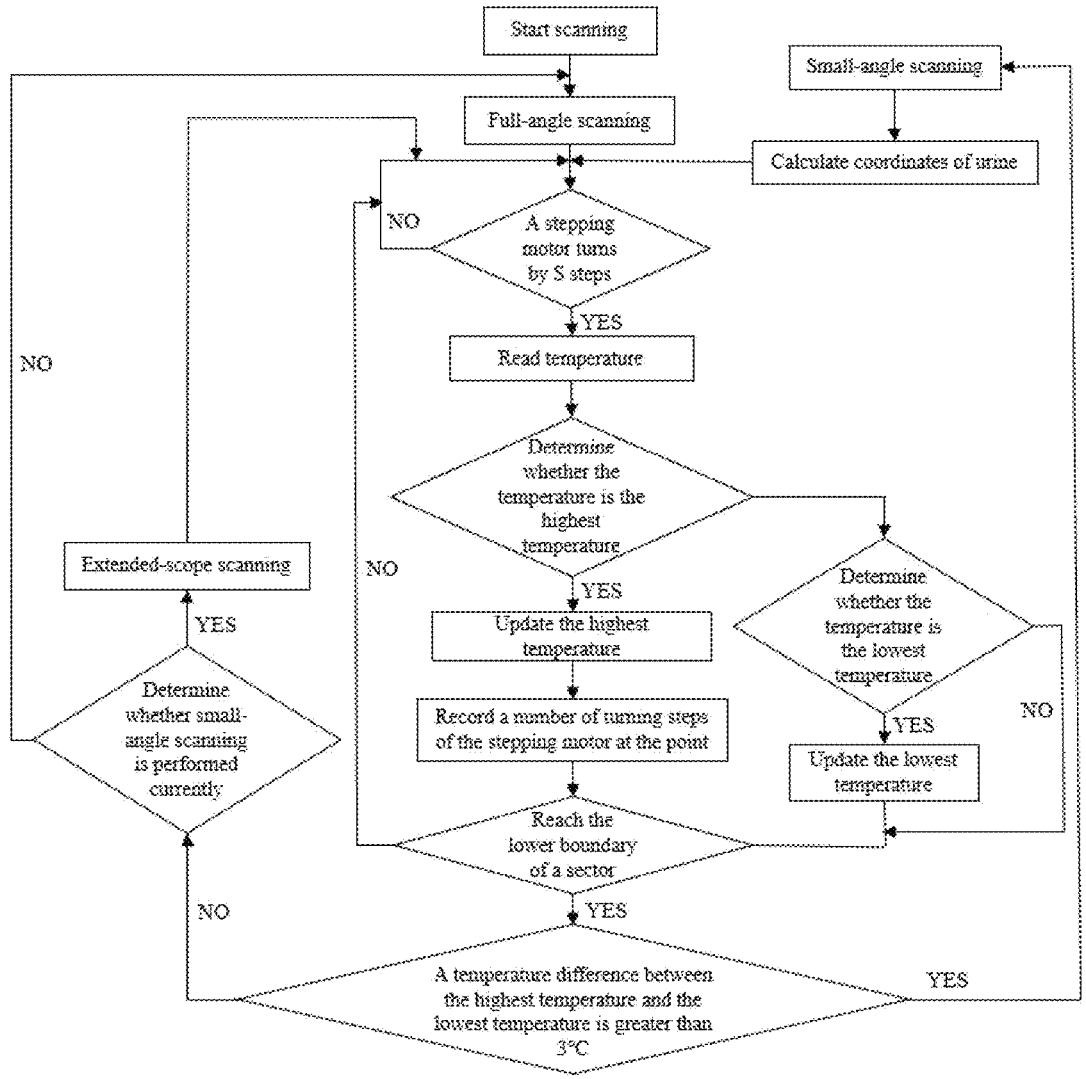
FIG. 8 is a control flowchart of a method according to a third embodiment.

A control flowchart of the entire method is shown in FIG. 8.

Embodiment 4

A sensor is mounted and fixed on the main shaft of a stepping motor, the sensor scans with the main shaft of the stepping motor within an angle $\gamma$, as shown in FIG. 2.

When the sensor scans within the angle $\gamma$ for the first time, temperature is read by the sensor each time the stepping motor turns by an angle $\varphi$, and the lowest temperature value is recorded. Environment temperature is calculated when the boundary of the angle $\gamma$ is reached, and the environment temperature is the lowest temperature. Different temperature difference thresholds are set according to different environment temperatures.

When the sensor scans within the angle $\gamma$ for the second and subsequent times, temperature is read once by the sensor each time the stepping motor turns by an angle $\varphi$, and the highest temperature value, the lowest temperature value and a turning angle $\lambda$ of the stepping motor at which the highest temperature value is read are recorded.

In the angle γ, every 5 degrees are defined as one sector, and the entire angle γ is divided into N sectors, as shown in FIG. 4.

A temperature difference between the highest temperature and the lowest temperature of the sector is calculated when the sensor reaches the lower boundary of a sector, as shown in FIG. 5. If the temperature difference is greater than the temperature difference threshold, the position of the urine is calculated. α=|γ/2−λ|, and X=(L1/COS μ)*TAN(|γ/2−λ|). Similarly, it can be calculated that β=|δ/2−ω|, and Y=(L2/COS ξ)*TAN(|δ/2−ω|).

When the position of the urine is changed, the sensor needs to re-determine the position of the urine.

The sensor has three modes comprising full-angle scanning, small-angle scanning and extended-scope scanning in the angle γ. The full-angle scanning reads temperature in the entire angle γ. The small-angle scanning reads temperature in the scope of a center sector and its adjacent sectors on both left and right sides, as shown in FIG. 6. The extended-scope scanning reads temperature in the scope of a center sector and its adjacent two sectors on both left and right sides, as shown in FIG. 7.

Before the position of the urine is found for the first time, the sensor conducts the full-angle scanning.

When the position of the urine is found, the sensor conducts the small-angle scanning in the scope of the sector where the urine is found and the adjacent sectors on both left and right sides.

When the sensor conducts the small-angle scanning, if none of the sectors presents a temperature difference greater than the temperature difference threshold, which indicates that the position of the urine is changed, the sensor conducts the extended-scope scanning in the scope of the sector where the urine is originally found and the adjacent two sectors on both left and right sides.

If none of the sectors presents a temperature difference greater than the temperature difference threshold during the extended-scope scanning, the sensor conducts a full-angle scanning again.

Figure 9:
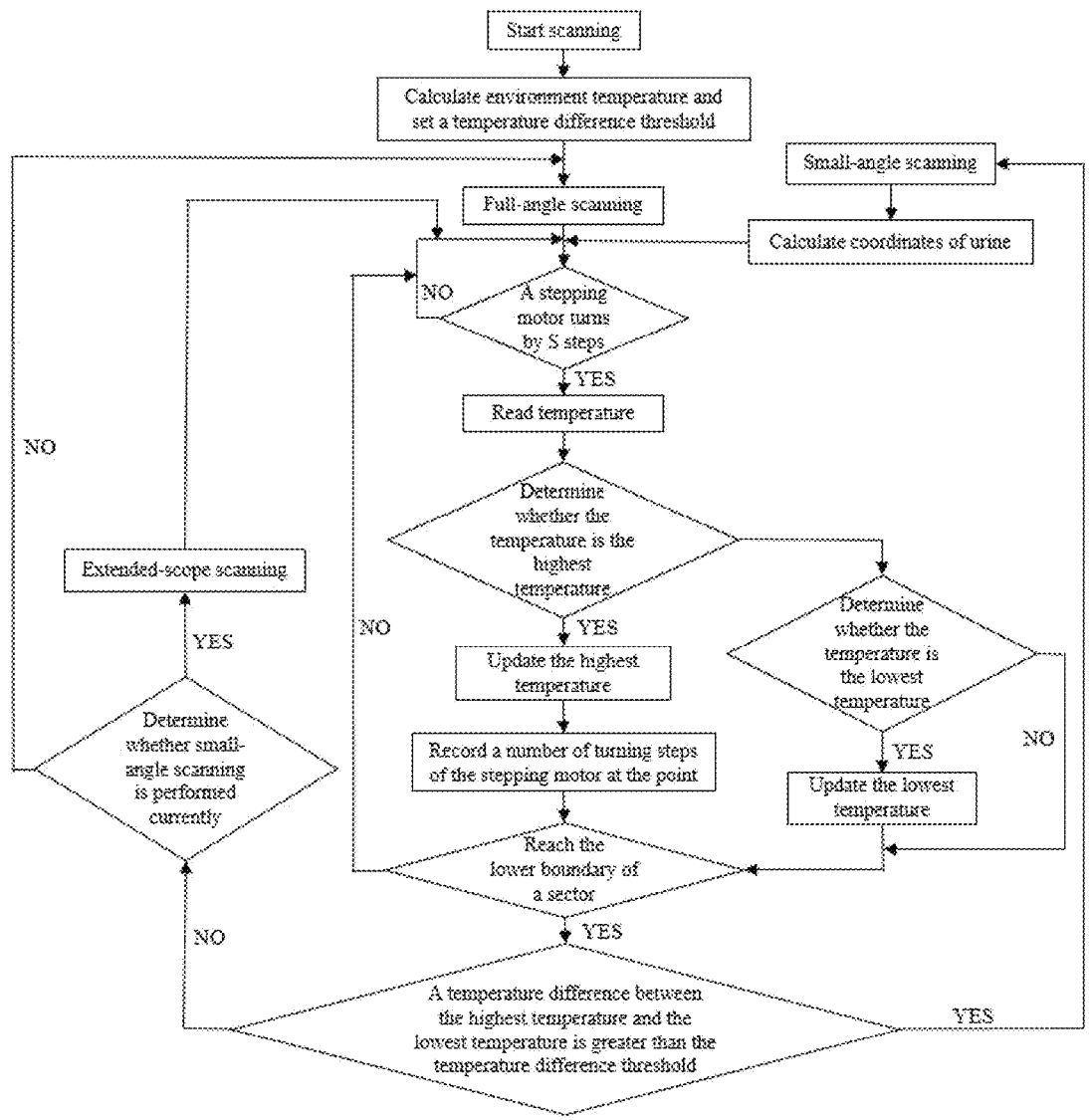
FIG. 9 is a control flowchart of a method according to a fourth embodiment.

A control flowchart of the entire method is shown in FIG. 9.

Embodiment 5 (as Shown in FIGS. 1 to 9)

A device for automatically positioning urine for a healthy smart toilet according to the present invention, in a sense of virtual module structure, the device comprises a module for automatically positioning urine configured to determine the position of urine according to a temperature result scanned by a non-contact temperature sensor and calculate point coordinates of the position of the urine in the toilet.

The above module for automatically positioning urine comprises:

a first module for scanning, recording and position calculating, configured to scan and detect temperature by sector scanning within an angle γ using a non-contact temperature sensor arranged in a left or right side wall of the toilet driven by a stepping motor, and calculate, based on the angle with the highest temperature and tangent formula, X in point coordinates (X, Y) of the position of the urine in the toilet; and/or a second module for scanning, recording and position calculating, configured to scan and detect temperature by sector scanning within an angle δ using the non-contact temperature sensor arranged in a front or rear side wall of the toilet and driven by a stepping motor, and calculate, based on the angle with the highest temperature and tangent formula, Y in point coordinates (X, Y) of the position of the urine in the toilet.

The above first module for scanning, recording and position calculating specifically comprises: a first module for scanning and recording, configured to read temperature by the sensor when the sensor scans within the angle γ each time the stepping motor turns by an angle φ, and to record the highest temperature value and the turning angle λ of the stepping motor at which the highest temperature value is read; and a first module for position calculating, configured to calculate the position of the urine when the sensor reaches the boundary of the angle γ; and the above second module for scanning, recording and position calculating specifically comprises: a second module for scanning and recording, configured to read temperature by the sensor when the sensor scans within the angle δ each time the stepping motor turns by an angle θ, and to record the highest temperature value and the turning angle ω of the stepping motor at which the highest temperature value is read; and a second module for position calculating, configured to calculate the position of the urine when the sensor reaches the boundary of the angle δ.

In the first module for position calculating of the first module for scanning, recording and position calculating, the calculation method is: X=(L1/COS μ)*TAN(|γ/2−λ|); wherein, L1 is the distance between the long shaft of the toilet and the central scanning point of the left or right side wall where the sensor is located.

In the second module for position calculating of the second module for scanning, recording and position calculating, the calculation method is Y=(L2/COS ξ)*TAN(|δ/2−ω|); wherein, L2 is the distance between the short shaft of the toilet and the central scanning point of the front or rear side wall where the sensor is located.

Preferably, in the first and second modules for scanning and recording, when the sensor reads temperature, the lowest temperature value is recorded meanwhile; and in the first and second modules for position calculating, each time the sensor reaches the boundary, a temperature difference between the highest temperature and the lowest temperature is calculated, and if the temperature difference is greater than a set temperature difference threshold, the position of the urine is calculated.

Preferably, in the first and second modules for scanning and recording, the entire scanning area is divided into N sectors; and in the first and second modules for position calculating, each time the sensor reaches the lower boundary of one sector, a temperature difference between the highest temperature and the lowest temperature of the sector is calculated, and if the temperature difference is greater than the set temperature difference threshold, the position of the urine is calculated.

Preferably, the device for automatically positioning urine further comprises a module for setting temperature difference threshold, wherein scanning is firstly conducted in the scope of the angle γ or angle δ, the lowest environment temperature in the scope of the angle γ or angle δ is recorded, and different temperature difference thresholds are set according to different lowest environment temperatures; or the temperature difference threshold is directly set as 3° C.

Preferably, in the module for automatically positioning urine, the sensor has three modes comprising full-angle scanning, small-angle scanning and extended-scope scanning in the angle γ and angle δ; the full-angle scanning reads temperature within the entire angle γ and angle δ; Each scanning area is divided into N sectors, the small-angle scanning reads temperature in the scope of a center sector and its adjacent sectors on both left and right sides; and the extended-scope scanning reads temperature in the scope of a center sector and its adjacent two sectors on both left and right sides; before the position of the urine is found for the first time, the sensor conducts the full-angle scanning; when the position of the urine is found, the sensor conducts the small-angle scanning in the scope of the sector where the urine is found and the adjacent sectors on both left and right sides; when the sensor conducts a small-angle scanning, if none of the sectors presents a temperature difference greater than the temperature difference threshold, which indicates that the position of the urine is changed, the extended-scope scanning is conducted by the sensor in the scope of the sector where the urine is originally found and adjacent two sectors on both left and right sides; and if none of the sectors presents a temperature difference greater than the temperature difference threshold during the extended-scope scanning, the sensor conducts a full-angle scanning again.

Embodiment 6

Figure 10:
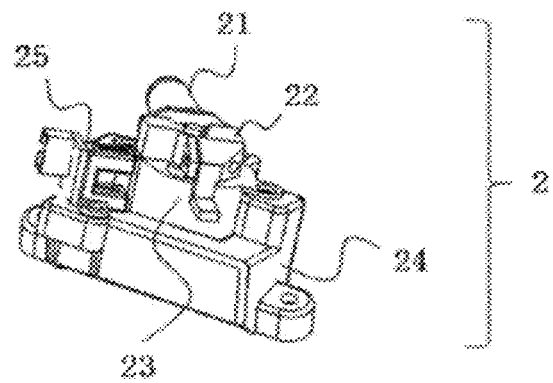
FIG. 10 and FIG. 11 are schematic diagrams of physical structures of a device for automatically positioning urine at different angles.
Figure 11:
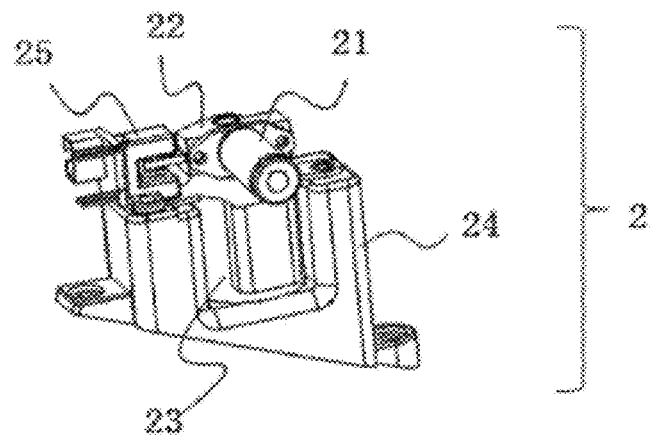

As shown in FIGS. 10 and 11, in a sense of physical structure, a device for automatically positioning urine according to the present invention comprises one or more sets of positioning assemblies 2; wherein the positioning assembly 2 comprises a non-contact temperature sensor 21, a stepping motor 23 and a motor frame 24; the non-contact temperature sensor may be an infrared temperature sensor, and may be fixed to the main shaft of the stepping motor 23 through a sensor fixing part 22, the stepping motor 23 is fixed to the motor frame 24, and the motor frame 24 is used for fixing to the toilet; and the stepping motor 23 can drive the non-contact temperature sensor 21 to conduct sector scanning.

The above positioning assembly 2 further comprises an optocoupler 25 connected to the non-contact temperature sensor 21 and used for determining a zero point of polar coordinates of the sensor.

Embodiment 7

Figure 12:
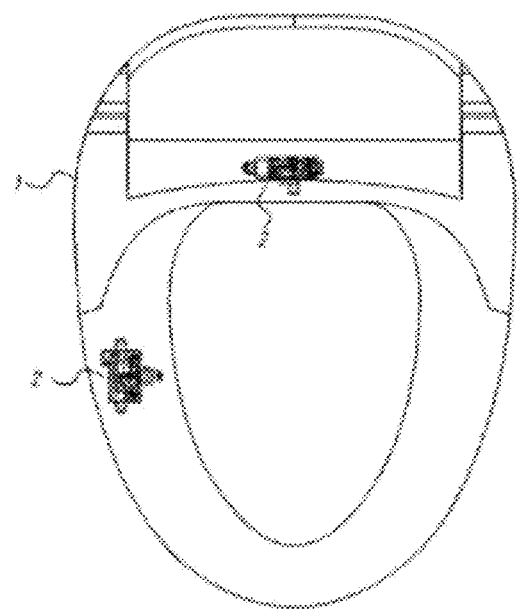
FIG. 12 is a schematic structure diagram of a healthy smart toilet containing the device for automatically positioning urine.

As shown in FIG. 12, a healthy smart toilet according to the present invention comprises a toilet body 1, and further comprises a device for automatically positioning urine, which is mounted on the toilet body 1, one or more sets of the positioning assemblies 2 as described in the embodiment 6 are used in the device for automatically positioning urine. The stepping motor 23 can drive the non-contact temperature sensor 21 to conduct sector scanning, and a certain included angle may be formed between a scanning plane and a horizontal plane, or a horizontal scanning may be directly conducted.

One set of the positioning assembly 2 may be provided, which is mounted on a left or right side wall of the toilet body 1, and more preferably, two sets of the positioning assemblies 2 may be provided, one set is mounted on a front or rear side wall of the toilet body 1, and the other set is mounted on the left or right side wall of the toilet body 1.

The foregoing description is merely preferred embodiments of the present invention, but is not intended to limit the present invention in any form, and any simple amendments, equivalent changes or modifications made by those skilled in the art using the technical contents disclosed above shall all fall within the protection scope of the present invention.

What is claimed is:

1. A method for automatically positioning urine, comprising:
   determining a position of the urine in response to a temperature scanned by a non-contact temperature sensor; and
   calculating point coordinates of the position of the urine in a toilet.

2. The method of claim 1, further comprising at least one of:
   step A, which comprises:
      scanning and detecting the temperature by sector scanning within an angle γ using the non-contact temperature sensor arranged in a left side wall or a right side wall of the toilet, wherein the non-contact temperature sensor is driven by a stepping motor; and
      calculating X in point coordinates (X, Y) of the position of the urine in the toilet based on the angle γ with a highest temperature and tangent formula; and
   step B, which comprises:
      scanning and detecting the temperature by sector scanning within an angle δ using the non-contact temperature sensor arranged in a front side wall or a rear side wall of the toilet, wherein the non-contact temperature sensor is driven by the stepping motor; and
      calculating Y in the point coordinates (X, Y) of the position of the urine in the toilet based on the angle δ with the highest temperature and tangent formula.

3. The method of claim 2, wherein the step A comprises:
   step A1, in which when the non-contact temperature sensor scans within the angle γ, the non-contact temperature sensor reads the temperature each time the stepping motor turns by an angle φ and records a highest temperature value and a turning angle λ of the stepping motor at which the highest temperature value is read; and
   step A2, in which calculating the position of the urine each time the non-contact temperature sensor reaches a boundary of the angle γ;
   wherein the step B comprises:
      step B1, in which when the non-contact temperature sensor scans within the angle δ, the non-contact temperature sensor reads the temperature each time the stepping motor turns by an angle θ and records the highest temperature value and a turning angle ω of the stepping motor at which the highest temperature value, is read; and
      step B2, in which calculating the position of the urine each time the non-contact temperature sensor reaches a boundary of the angle δ.

4. The method of claim 3, wherein:
   in the step A2, a calculation method is X=(L1/COS μ)*TAN(|γ/2−λ|), wherein L1 is a distance between a long shaft of the toilet and a central scanning point of the left side wall or the right side wall where the non-contact temperature sensor is located, and μ is an included angle between a first scanning plane of the non-contact temperature sensor and a first horizontal plane; and
   in the step B2, a calculation method is Y=(L2/COS ξ)*TAN(|δ/2−ω|), wherein L2 is a distance between a short shaft of the toilet and a central scanning point of the front side wall or the rear side wall where the non-contact temperature sensor is located, and ξ is an included angle between a second scanning plane of the non-contact temperature sensor and a second horizontal plane.

5. The method of claim 3, wherein:
in the steps A1 and B1, when the non-contact temperature sensor reads the temperature, a lowest temperature value is, recorded meanwhile; and
in the steps A2 and B2, each time the non-contact temperature sensor reaches the boundary of the associated angle, a temperature difference between the highest temperature and the lowest temperature is calculated, such that the position of the urine is calculated if the temperature difference is greater than a set temperature difference threshold.

6. The method of claim 5, wherein:
in the steps A1 and B1, a scanning area is divided into N sectors; and
in the steps A2 and B2, each time the non-contact temperature sensor reaches a lower boundary of one sector of the N sectors, a temperature difference between the highest temperature and the lowest temperature of the one sector is calculated, and the position of the urine is calculated if the temperature difference is greater than the set temperature difference threshold.

7. The method of claim 5, wherein:
prior to step A, scanning is firstly conducted in a scope of the angle $\gamma$ or the angle $\delta$, a lowest environment temperature in the scope of the angle $\gamma$ or the angle $\delta$ is recorded, and different temperature difference thresholds are set in response to different lowest environment temperatures; or
the temperature difference threshold is directly set as 3° C.

8. The method of claim 5, wherein:
the non-contact temperature sensor has three modes comprising full-angle scanning, small-angle scanning, and extended-scope scanning, in the angle $\gamma$ and the angle $\delta$; the full-angle scanning reads the temperature over all of the angle $\gamma$ and the angle $\delta$; a scanning area is divided into N sectors, the small-angle scanning reads the temperature in a scope of a center sector and its adjacent sectors on both left and right sides; and the extended-scope scanning reads the temperature in the scope of the center sector and its adjacent two sectors on both left and right sides;
before the position of the urine is found for the first time, the non-contact temperature sensor conducts the full-angle scanning;
after the position of the urine is found, the non-contact temperature sensor conducts the small-angle scanning in the scope of the sector where the urine is found and the adjacent sectors on both left and right sides;
when the non-contact temperature sensor conducts the small-angle scanning, if none of the sectors presents the temperature difference greater than the set temperature difference threshold, which indicates that the position of the urine is changed, the extended-scope scanning is conducted by the non-contact temperature sensor in the scope of the sector where the urine is originally found and the adjacent two sectors on both left and right sides; and
if none of the sectors presents the temperature difference greater than the set temperature difference threshold during the extended-scope scanning, the non-contact temperature sensor conducts the full-angle scanning again.

9. A device for automatically positioning urine, comprising:
a module that is configured to determine a position of the urine in response to a temperature scanned by a non-contact temperature sensor, and is configured to calculate point coordinates of the position of the urine in a toilet.

10. The device of claim 9, wherein the module comprises at least one of:
a first module for scanning, recording and position calculating, wherein the first module is configured to scan and detect the temperature by sector scanning within an angle $\gamma$ using the non-contact temperature sensor arranged in a left side wall or a right side wall of the toilet, wherein the non-contact temperature sensor is, driven by a stepping motor, and the first module calculates X in point coordinates (X, Y) of the position of the urine in the toilet based on the angle $\gamma$ with a highest temperature and tangent formula; and
a second module for scanning, recording and position calculating, wherein the second module is configured to scan and detect the temperature by sector scanning within an angle $\delta$ using the non-contact temperature sensor arranged in a front side wall or a rear side wall of the toilet, wherein the non-contact temperature sensor is driven by the stepping motor, and the second module calculates V in the point coordinates (X, Y) of the position of the urine in the toilet based on the angle $\delta$ with the highest temperature and tangent formula.

11. The device of claim 10, wherein:
the first module comprises:
a first scanning and recording module configured to read the temperature once by the non-contact temperature sensor when the non-contact temperature sensor scans within the angle $\gamma$ each time the stepping motor turns by an angle $\varphi$, and record a highest temperature value and a turning angle $\lambda$ of the stepping motor at which the highest temperature value is read; and
a first position calculating module configured to calculate the position of the urine when the non-contact temperature sensor reaches a boundary of the angle $\gamma$; and
the second module comprises:
a second scanning and recording module configured to read temperature once by the non-contact temperature sensor when the non-contact temperature sensor scans within the angle $\delta$ each time the stepping motor turns by an angle $\theta$, and record the highest temperature value and a turning angle $\omega$ of the stepping motor at which the highest temperature value is read; and
a second position calculating, module configured to calculate the position, of the urine when the non-contact temperature sensor reaches a boundary of the angle $\delta$.

12. The device of claim 11, wherein:
the first position calculating module uses a calculation method that is $X=(L1/COS\ \mu)*TAN(|\gamma/2-\lambda|)$, wherein L1 is a distance between a long shaft of the toilet and a central scanning point of the left side wall or the right side wall where the non-contact temperature sensor is located, and $\mu$ is an included angle between a first scanning plane of the non-contact temperature sensor and a first horizontal plane; and
the second position calculating module uses a calculation method that is $Y=(L2/COS\ \xi)*TAN(|\delta/2-\omega|)$, wherein L2 is a distance between a short shaft of the toilet and a central scanning point of the front side wall or the rear side wall where the non-contact temperature sensor is located, and ξ is an included angle between a first scanning plane of the non-contact temperature sensor and a second horizontal plane.

13. The device of claim 11, wherein:
in the first and second scanning and recording modules, when the non-contact temperature sensor reads the temperature, a lowest temperature value is recorded meanwhile; and
in the first and second position calculating modules, each time the non-contact temperature sensor reaches the boundary of the associated angle, a temperature difference between the highest temperature and the lowest temperature is calculated, such that the position of the urine is calculated if the temperature difference is greater than a set temperature difference threshold.

14. The device of claim 13, wherein:
in the first and second scanning and recording modules, a scanning area is divided into N sectors; and
in the first and second position calculating modules, when the non-contact temperature sensor reaches a lower boundary of one sector of the N sectors, a temperature difference between the highest temperature and the lowest temperature of the one sector is calculated, and the position of the urine is calculated if the temperature difference is greater than the set temperature difference threshold.

15. The device of claim 13, further comprising a temperature difference module for setting the set temperature difference threshold, wherein in the temperature difference module, scanning is firstly conducted in a scope of the angle γ or the angle δ, the lowest environment temperature in the scope of the angle γ or the angle δ is recorded, and different temperature difference thresholds are set in response to different lowest environment temperatures; or the set temperature difference threshold is directly set as 3° C.

16. The device of claim 13, wherein:
in the module, the non-contact temperature sensor has three modes comprising full-angle scanning, small-angle scanning, and extended-scope scanning, in the angle γ and the angle δ; the full-angle scanning reads temperature over an entirety of the angle γ and the angle δ; a scanning area is divided into N sectors, the small-angle scanning reads the temperature in a scope of a center sector and its adjacent sectors on both left and right sides; and the extended-scope scanning reads the temperature in the scope of the center sector and its adjacent two sectors on both left and right sides;
before the position of the urine is found for the first time, the non-contact temperature sensor conducts the full-angle scanning;
after the position of the urine is found, the non-contact temperature sensor conducts the small-angle scanning in the scope of the sector where the urine is found and the adjacent sectors on both left and right sides;
when the non-contact temperature sensor conducts the small-angle scanning, if none of the sectors presents the temperature difference greater than the set temperature difference threshold, which indicates that the position of the urine is changed, the extended-scope scanning is conducted by the non-contact temperature sensor in the scope of the sector where the urine is originally found and the adjacent two sectors on both left and right sides; and
the sensor conducts the full-angle scanning again if none of the sectors presents the temperature difference greater than the temperature difference threshold during the extended-scope scanning.

17. A device for automatically positioning urine, comprising:
at least one positioning assembly, wherein each positioning assembly comprises a non-contact temperature sensor, a stepping motor, and a motor frame;
wherein the non-contact temperature sensor is fixed to a main shaft of the stepping motor, the stepping motor is fixed to the motor frame, and the motor frame is configured to be fixedly coupled to a toilet; and
wherein the stepping motor can drive the non-contact temperature sensor to conduct sector scanning.

18. The device of claim 17, wherein each positioning assembly further comprises an optocoupler connected to the non-contact temperature sensor and configured to determine a zero point of polar coordinates of the non-contact temperature sensor.

19. A healthy smart toilet, comprising:
a toilet body; and
the device of claim 18;
wherein the device is mounted on the toilet body, and the stepping motor can drive the non-contact temperature sensor to conduct sector scanning of the toilet body.

20. The healthy smart toilet of claim 19, wherein the at least one positioning assembly comprises:
a first positioning assembly mounted on a front side wall or a rear side wall of the toilet body, and
a second positioning assembly mounted on a left side wall or a right side wall of the toilet body.

* * * * *